United States Patent [19]

Minai

[11] 4,335,263
[45] Jun. 15, 1982

[54] PROCESS FOR PREPARING AROMATIC ALDEHYDES

[75] Inventor: Masayoshi Minai, Moriyama, Japan

[73] Assignee: Sumitomo Chemical Company, Limited, Osaka, Japan

[21] Appl. No.: 218,135

[22] Filed: Dec. 19, 1980

[30] Foreign Application Priority Data

Dec. 21, 1979 [JP] Japan ................. 54/167013

[51] Int. Cl.³ ............... C07C 45/43; C07C 37/01
[52] U.S. Cl. ................. 568/437; 568/771; 568/800; 568/803; 568/319; 568/322; 568/649; 568/652; 549/362; 549/436
[58] Field of Search ............ 568/319, 322, 771, 803, 568/809, 437, 652, 678, 649; 260/340.3, 340.5 R

[56] References Cited

U.S. PATENT DOCUMENTS 2,816,144 12/1957 Harris .................. 568/437
3,360,566 12/1967 Linder et al. .
3,585,243 6/1971 Gradeff ................ 568/803
4,008,276 2/1977 Zenitz ................. 568/319

FOREIGN PATENT DOCUMENTS 11281 11/1979 European Pat. Off. .......... 568/437
2101992 8/1972 Fed. Rep. of Germany ...... 568/771
49-14213 4/1974 Japan .................. 568/437

OTHER PUBLICATIONS

House, Modern Synth. Rxns., W A. Benjamin, Inc., pp. 797–809, (1972).
Haslam, Procective Groups in Org. Synthesis, pp. 149–157, (1976).
Buehler et al., Survey of Org. Synthesis, vol. 2, John Wiley and Sons, pp. 511, 561–562, (1979).

Primary Examiner—Natalie Trousof
Assistant Examiner—James H. Reamer
Attorney, Agent, or Firm—Sughrue, Mion, Zinn, Macpeak & Seas

[57] ABSTRACT

A process for preparing an aromatic aldehyde represented by the following general formula:

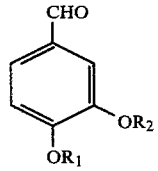

wherein $R_1$ and $R_2$ each represents a hydrogen atom or a lower alkyl group or $R_1$ and $R_2$ may jointly form an alkylene group, provided that $R_1$ and $R_2$ do not represent a hydrogen atom at the same time.

15 Claims, No Drawings

PROCESS FOR PREPARING AROMATIC ALDEHYDES

FIELD OF THE INVENTION

This invention relates to a novel process for preparing aromatic aldehydes represented by the following general formula (IX):

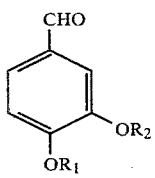
(IX)

wherein $R_1$ and $R_2$ each represents a hydrogen atom or a lower alkyl group or $R_1$ and $R_2$ may jointly form an alkylene group, provided that $R_1$ and $R_2$ do not represent a hydrogen atom at the same time.

BACKGROUND OF THE INVENTION

The aromatic aldehydes represented by the above general formula (IX) are used as perfumes (for example, heliotropin, veratraldehyde, etc.), or are important intermediates for medicines, agricultural chemicals, etc.

An object of the present invention is to provide a process for preparing such aromatic aldehydes inexpensively with industrial advantages.

As the conventional process for preparing the aromatic aldehydes represented by the general formula (IX), for example, heliotropin (piperonal), there is known a process of isomerizing and oxidizing in which safrole contained in the essential oil of Octoea Cymbarum is used as the starting material (disclosed in U.S. Pat. No. 2,916,499). However, this process has the defect that the supplied amount and the price of the starting material are unstable due to its dependence upon the natural world and involves problems about safety of safrole or isosafrole. Thus, processes using synthetic chemicals as starting materials have been demanded.

As one of such processes, there is known a process of using, as a starting material, methylenedioxybenzene which is prepared from pyrocatechol. This methylenedioxybenzene is directly formylated [process (1): Japanese patent application (OPI) No. 156867/77 (the term "OPI" as used herein refers to a "published unexamined Japanese patent application")], chloromethylated [process (2): *J. Gen. Chem.*, 8, 975 (1938) and British Pat. No. 1,538,214], or converted to a mandelic acid type compound [process (3): Belgian Pat. No. 877,911, German Pat. No. 2,754,490 and *Current Sci.*, (India) 27, 22 (1958)].

However, process (1) has the defects that N-methylformanilide is not inexpensive, that N-methylaniline formed as a by-product from N-methylformanilide is recovered only in low yield, and that formic acid must be used for preparing N-methylformanilide from N-methylaniline, thus being unsatisfactory as an industrial process. Further, 50 to 60% of 1,2-methylenedioxybenzene is recovered in an unreacted state, and hence an energy loss is so serious that it is disadvantageous as an industrial process.

Process (2) has such defects as that it provides the end product in a yield as low as 55 to 60% based on methylenedioxybenzene, that a large amount of a tar-like material is formed as a by-product, that it requires complicated reaction procedures, and that a metal hydroxide formed as a by-product must be properly treated.

Process (3) has such defects as that glyoxalic acid used as one of the starting materials is expensive, that it requires to use a heavy metal like a copper catalyst in the step of converting the intermediate mandelic acid type compound to the aldehyde, and that the end product is produced only in low yield.

In any of these processes, 2,3-methylenedioxybenzaldehyde is formed as a by-product in addition to the end product, and hence there is a problem that separation and purification of the end product from the reaction product is difficult.

In this situation, the inventor has investigated a novel process for preparing aromatic aldehyde derivatives represented by the general formula (IX) as described above and, as a result, has discovered an extremely advantageous process which follows an absolutely different route from the conventional routes, which removes the defects with the conventional processes, which provides the end product in high yield and in high purity, and which involves steps easily put into industrial practice, thus having achieved the present invention.

SUMMARY OF THE INVENTION

An object of the present invention is to provide a process for preparing aromatic aldehydes represented by the general formula (IX):

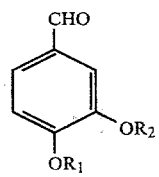
(IX)

wherein $R_1$ and $R_2$ each represents a hydrogen atom or a lower alkyl group or $R_1$ and $R_2$ may jointly form an alkylene group, provided that $R_1$ and $R_2$ do not represent a hydrogen atom at the same time, which comprises the following steps 1 to 5, steps 2 to 5, steps 3 to 5, or steps 4 to 5: [Step 1]

A step of directly condensing m- and/or p-cresol represented by the following formula (I):

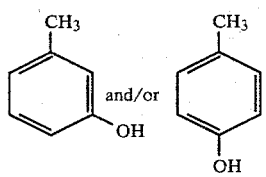
(I)

with an acetic acid derivative represented by the following general formula (II):

$CH_3COA$ (II)

wherein A represents a hydroxy group, a halogen atom, or $-OCOCH_3$, to obtain methylhydroxyacetophenone represented by the following formula (III):

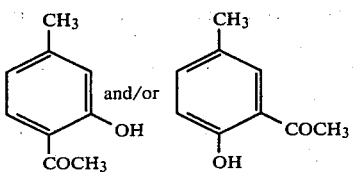

(III)

or reacting the compound (I) with the compound (II) to form methylphenyl acetate represented by the following formula (IV):

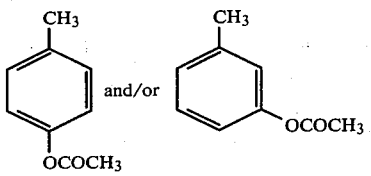

(IV)

and rearranging into the methylhydroxyacetophenone represented by the formula (III). [Step 2]

A step of oxidizing the compound (III) obtained in step 1 under alkaline condition to obtain 4-methylcatechol represented by the following formula (V):

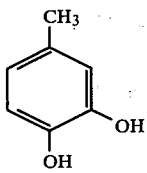

(V)

[Step 3]

A step of condensing the compound (V) obtained in step 2 with an alkylating agent to obtain a methylbenzene derivative represented by the following general formula (VI):

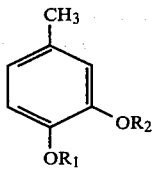

(VI)

wherein $R_1$ and $R_2$ each represents a hydrogen atom or a lower alkyl group or $R_1$ and $R_2$ may jointly form an alkylene group, provided that $R_1$ and $R_2$ do not represent a hydrogen atom at the same time. [Step 4]

A step of halogenating the compound (VI) obtained in step 3 to obtain a halide compound represented by the following general formula (VII) and/or (VIII):

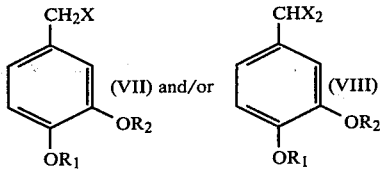

wherein $R_1$ and $R_2$ are the same as defined above, and X represents a halogen atom. [Step 5]

A step of oxidizing and/or hydrolyzing the compound (VII) and/or (VIII) obtained in step 4 to obtain an aromatic aldehyde represented by the following general formula (IX):

(IX)

wherein $R_1$ and $R_2$ are the same as defined above.

DETAILED DESCRIPTION OF THE INVENTION

The present invention will be described in more detail below.

2-Hydroxy-4-methylacetophenone and/or 2-hydroxy-5-methylacetophenone represented by the formula (III) can be prepared by directly condensing m- or p-cresol represented by the formula (I), or a mixture thereof, with an acetic acid derivative represented by the formula (II) (for example, acetic acid, acetyl chloride or bromide, acetic anhydride, etc.) in the presence of an acidic catalyst, or by reacting the compound (I) with the compound (II) in the presence or absence of an acidic or basic catalyst to form m- and/or p-methylphenyl acetate represented by the formula (IV), followed by rearrangement in the presence of an acidic catalyst.

In the former reaction, the compound (II) is usually used in an amount of 0.5 to 3 mols in terms of acetyl group per mol of m- and/or p-cresol. However, if the compound (II) is used too much, the resulting compound (III) can be further acetylated, and hence the compound (II) is preferably used in an amount of not more than 1.5 mols per mol of m- and/or p-cresol. In this reaction, unreacted compound (I) or (II) can be reused by separating and recovering from the reaction system after completion of the reaction.

In practicing this reaction, there are used as reaction solvents those which are generally used for Friedel-Crafts reaction, such as carbon disulfide, nitrobenzene, chlorobenzene, tetrachloroethane, dichloroethane, carbon tetrachloride, petroleum benzin, etc. These solvents can be used alone or as admixtures thereof. It is also possible to use the compound (I) as a solvent.

As the acidic catalyst which can be used, there are illustrated those which are ordinarily used for Friedel-Crafts reaction, such as aluminum chloride, aluminum bromide, ferric chloride, zinc chloride, stannic chloride, titanium chloride, silver perchlorate, polyphosphoric acid, etc. These are usually used in an amount of 0.1 to 4 mols, preferably 0.2 to 2.5 mols, per mol of the starting materials.

The reaction temperature can be optionally selected between 0° C. and 200° C., with 20° C. to 170° C. being preferable.

The compound (III) can be obtained in good yield from the thus-obtained reaction mixture through general procedures such as extraction, concentration, distillation, crystallization, etc. However, isolation and purification of the compound (III) are not always necessary for obtaining the compound (V) in the subsequent step, and the reaction mixture per se can be used in the subsequent step.

In the latter reaction via the methylphenyl acetate, an ordinary esterification process is applied to the synthesis of m- and/or p-methylphenyl acetate of the formula (IV). That is, in the case of using acetic acid as the acetic acid derivative represented by the formula (II), it is reacted with m- and/or p-cresol represented by the formula (I) in the presence of an acidic catalyst to form the ester. As the acidic catalyst which can be used, there are illustrated, for example, hydrochloric acid, sulfuric acid, boron trifluoride, p-toluenesulfonic acid, etc. The reactants are usually used in equimolar amounts, but either of them can be used in an excess amount, with the excess reactant being reused by recovering after completion of the reaction. As the solvent which can be used, any solvent can be used unless it does not react with the reactants, but those capable of azeotropically removing water to be formed as a result of the reaction are preferable. It is also possible to use either of the reactants in an excess amount as a solvent. The reaction temperature is usually 0° to 200° C., preferably 30° to 150° C.

In the case of using an acetyl halide such as acetyl chloride or acetyl bromide as the acetic acid derivative of the formula (II), esterification is conducted by condensing m- and/or p-cresol with the acetyl halide in the copresence of an acid-binding agent and in the presence or absence of an inert solvent. The acetyl halide is used in an amount of 0.8 to 1.5 mols, preferably 1.0 to 1.3 mols, per mol of m- and/or p-cresol. As the reaction solvent, there are illustrated, for example, hydrocarbons, aromatic hydrocarbons, halogenated hydrocarbons, etc. These solvents are not particularly limited as long as they do not react with the reactants. It is also possible to use no solvents. As the acid-binding agent which can be used, there are illustrated, for example, pyridine, triethylamine, trimethylamine, tributylamine, sodium carbonate, sodium hydrogencarbonate, etc. These are used usually in amounts of 1 to 4 mols, preferably 1.1 to 2.0 mols, per mol of the reactants.

The reaction temperature is in the range of from 0° to 150° C., preferably from 0° to 100° C.

In the case of using acetic anhydride as the acetic acid derivative of the formula (II), esterification can be easily conducted by treating at least 0.5 mol, per mol of m- and/or p-cresol, of acetic anhydride in the presence or absence of an acidic or basic catalyst at 0° C. to 150° C., preferably 30° to 130° C. In this case, solvents are not always necessary, and acetic anhydride may be used in an excess amount to function as a solvent. In using a catalyst, the same catalyst as used for the esterification using acetic acid or acetyl halide as a reactant may be used as well.

Alternatively, methylphenyl acetate can easily be synthesized by reacting m- and/or p-cresol with acetic anhydride in an alkaline aqueous solution.

Methylphenyl acetate of the formula (IV) can be obtained in good yield from the thus-obtained reaction mixture through general procedures such as extraction, concentration, distillation, etc. In some cases, the reaction mixture can be subjected to the subsequent rearrangement reaction without isolating methylphenyl acetate.

The thus-obtained compound (IV) can be converted to the compound (III) by the rearrangement in the presence of an acidic catalyst. As the reaction solvent which can be used, there are used those which are generally used for Friedel-Crafts reaction, such as carbon disulfide, nitrobenzene, chlorobenzene, tetrachloroethane, dichloroethane, carbon tetrachloride, petroleum benzin, etc., alone or in combination. Of these, chlorobenzene, tetrachloroethane and toluene are preferred. Also, the reaction can be conducted in the absence of a solvent.

As the acidic catalyst which can be used, there are illustrated those which are generally used for Friedel-Crafts reaction, such as aluminum chloride, aluminum bromide, ferric chloride, zinc chloride, stannic chloride, titanium chloride, perchloric acid, polyphosphoric acid, etc. These are used in amounts of 0.1 to 4 mols, preferably 0.2 to 2.5 mols, per mol of the reactants.

The reaction temperature is optionally selected between 0° and 250° C., preferably 10° to 200° C., most preferably 80° to 160° C.

The compound (III) can be obtained in good yield from the thus-obtained reaction mixture through the procedures of extraction, concentration, distillation, crystallization, etc. However, isolation and purification of the compound (III) are not always necessary for obtaining the compound (V) in the subsequent step, and the reaction mixture may be subjected per se to the subsequent step.

In the oxidation reaction (step 2) of obtaining 4-methylcatechol of the formula (V) from methylhydroxyacetophenone of the formula (III), reaction of hydrogen peroxide under alkaline condition, generally called Dakin reaction, is selected.

As the reaction solvent which can be used, there are illustrated water, water-soluble solvents such as dioxane, tetrahydrofuran, methanol, n-propyl alcohol, isopropyl alcohol, ethylene glycol, acetone, dimethylformamide, dimethyl sulfoxide, etc., or a heterogeneous mixture solvent of a water-insoluble or slightly water-soluble organic solvent (e.g., benzene, toluene, chloroform, dichloromethane, carbon tetrachloride, diethyl ether, methyl isobutyl ketone, chlorobenzene, dichlorobenzene, tetrachloroethane, hexane, petroleum benzin, methyl n-propyl ketone, amyl alcohol, etc.) and water.

In the case that the heterogeneous mixture solvent is used, use of a catalyst is preferable from the viewpoint of product yield. In this case, there are such advantages as that separation of the product from the reaction solution is easy as compared to the case that water or the water-soluble solvent is used, and that isolation and recovery of the solvent used for the separation and purification (by extraction) of the product and the solvent used for the reaction are not necessary because the organic solvent used also functions as an extracting solvent.

In this reaction, the alkali is usually used in an amount of 1 to 1.5 mols per mol of starting methylhydroxyacetophenone, with more than 1.5 mols being also employable. Hydrogen peroxide is preferably used in an amount of from 1 to 1.5 mols per mol of methylhydroxyacetophenone, with more than 1.5 mols being employable, too.

As the alkali which can be used, there are illustrated, for example, alkali metal hydroxides, alkali metal carbonates, alkaline earth metal hydroxides, etc.

In this reaction, addition of a catalyst such as organic quaternary ammonium salts, phosphonium salts, tertiary amines, pyridines, or various surfactants (e.g., alkylbenzenesulfonates, etc.) in a catalytic amount comparatively improves the reaction rate and increases the conversion, thus the use thereof being preferable. As the organic quaternary ammonium salts and tertiary amines, there are illustrated tetra-n-butylammonium chloride (or bromide or hydroxide), tetraethylammonium chloride (or bromide or hydroxide), triethylbenzylammonium chloride (or bromide or hydroxide), tricaprylmethylammonium chloride (or bromide), capryltrimethylammonium chloride (or bromide), dodecyltrimethylammonium chloride (or bromide), caprylbenzyldimethylammonium chloride (or bromide or hydroxide), triethylamine, trimethylamine, tributylamine, etc. As the phosphonium salts, there are illustrated tetraphenylphosphonium chloride (or bromide), tetrabutylphosphonium chloride (or bromide), tricaprylethylphosphonium chloride (or bromide), etc. As the pyridines, there are illustrated pyridine, α-, β- or γ-picoline, 2,4-lutidine, 2,6-lutidine, etc. As the alkylbenzenesulfonates, there are illustrated sodium caprylbenzenesulfonate, sodium dodecylbenzenesulfonate, etc. These are used alone or in combination. The amount of the catalyst is not particularly limited but, usually, it is in the range of from about 1/200 to about 2 mols, preferably about 1/100 to ½ mol, per mol of the methylhydroxyacetophenone of the formula (III).

The catalyst used can be reused by recovering after completion of the reaction.

The reaction temperature is optionally selected between −20° and 100° C., with 0° to 60° C. being preferable.

The compound (V) can be obtained in good yield from the thus-obtained reaction mixture through the procedures of liquid separation, concentration, distillation, crystallization, etc. However, isolation of the compound of the formula (V) is not always necessary to obtain the compound of the formula (VI) in the subsequent step, and the reaction mixture per se may be subjected to the subsequent step.

The reaction of obtaining the methylbenzene derivative represented by the formula (VI) from 4-methylcatechol of the formula (V) [step 3] is conducted generally by reaction 4-methylcatechol with various alkylating agents in the presence of an alkali.

This reaction provides the ether derivative of 4-methylcatechol generally by reacting with various alkylating agents in the presence of an alkali.

As the alkali which can be used, there are illustrated, for example, alkali metal hydroxides, alkali metal carbonates, alkaline earth metal hydroxides, etc.

These alkalis are used in optional amounts of not less than 0.7 mol per mol of 4-methylcatechol of the formula (V). In order to obtain a mono-substituted ether, they are used in amounts of 0.7 to 1.5 mols and, in order to obtain a di-substituted ether, they are used in amounts of 2 to 2.5 mols, per mol of 4-methylcatechol, respectively. However, the alkalis in amounts higher than the above-specified amounts are also employable.

As the alkylating agent, there are illustrated, for example, alkylsulfates (e.g., dimethylsulfate, diethylsulfate, methylenesulfate, etc.), halogenated hydrocarbons (e.g., methyl chloride (or bromide or iodide), ethyl chloride (or bromide or iodide), n-(or iso-)propyl chloride (or bromide or iodide), n-(or iso- or tert-)butyl chloride (or bromide or iodide), methylene or ethylene chloride (or bromide or iodide), propylene chloride (or bromide or iodide), etc.), and alkyl toluenesulfonates (e.g., methyl tosylate, ethyl tosylate, propyl tosylate, butyl tosylate, etc.).

These alkylating agents are used in optional amounts of 1 mol or more per mol of 4-methylcatechol. In order to obtain a mono-substituted ether, they are preferably used in amounts of 1 to 1.5 mols and, in order to obtain a di-substituted ether, they are preferably used in amounts of 2 to 2.5 mols, per mol of the reactant, respectively.

Additionally, presence of an organic quaternary ammonium salt or a tertiary amine as a catalyst permits the reaction to proceed at a comparatively low temperature with an improved reaction rate, thus being extremely effective. As to the examples and amounts of the catalyst, the same as described in the preceding step 2 applies.

As the reaction solvent, those described in the step 2 are used. The reaction temperature is optionally selected between −20° and 200° C., with 0° to 170° C. being preferable.

The compound of the formula (VI) can also be obtained by the condensation reaction between 4-methylcatechol and various alcohols. In this case, 4-methylcatechol and a lower alcohol are subjected to dehydration condensation in the presence or absence of an acidic catalyst.

This reaction is applied to the synthesis of disubstituted ethers. The lower alcohol is used in an optional amount of 2 mols or more per mol of 4-methylcatechol, with 2 to 10 mols being preferable. In this situation, it is possible to use an excess alcohol as a solvent. As the acidic catalyst which can be used, there are illustrated, for example, boron trifluoride, boric acid, alumina, acetic anhydride, sulfuric acid, hydrochloric acid, toluenesulfonic acid, phosphorus pentoxide, etc.

The reaction temperature is in the range of from 0° to 400° C. depending upon the kind of alcohol used. The reaction can also be conducted at suitable temperatures higher than the boiling point of the alcohol under pressure.

The compound of the formula (VI) can be obtained in good yield from the thus-obtained reaction mixture through the procedures of extraction, concentration, distillation, etc. However, isolation and purification of the compound (VI) are not particularly necessary for obtaining the compound of the formula (VII) and/or (VIII) in the subsequent step, and the reaction mixture per se may be subjected to the subsequent step.

The reaction of obtaining a halide compound represented by the formula (VII) and/or (VIII) by halogenating the compound of the formula (VI) (step 4) is conducted usually by reacting with a halogen or a halide compound in the presence of a catalyst as a radical-generating agent or under irradiation with light.

As the catalyst which can be used, there are illustrated, for example, free radical-generating agents such as azobisisobutyronitrile, peroxides (e.g., benzoyl peroxide, t-butyl perbenzoate, etc.), and the like and, as the light source for the irradiation, there are illustrated a mercury vapor lamp, sunlight, etc. The amount of the catalyst used is not particularly limited but, usually, it is in the range of ½ to 1/1,000 mol, preferably 1/10 to 1/500 mol, per mol of the compound (VI). Further, as a promotor, there can be used bases such as potassium carbonate, sodium carbonate, sodium hydrogencarbonate, potassium hydrogencarbonate, pyridine, etc., as an acid-binding agent or for the purpose of depressing side reactions. As the halogen or halide compound (hereinafter inclusively referred to as halogen), there are illustrated, for example, chlorine, bromine, iodine, N-bromosuccinimide, carbon tetrabromide, phosphorus trichloride, etc., with bromine being preferred.

The halogen is used in an optional amount of 0.4 to 2.4 mols per mol of the compound of the formula (VI), with 0.5 to 1.8 mols being preferable. Where the halogen is used in an amount of 0.4 to 1.3 mols per mol of the compound (VI), there results a benzyl halide as a main product and, where it is used in a more amount, there results a benzal halide as a main product.

As the solvent, there are illustrated those which are inert to the halogen, such as halogenated hydrocarbons (e.g., carbon tetrachloride, tetrachloroethane, chlorobenzene, dichloroethane, methyl chloroform, dichlorobenzene, hexachloroethane, etc.), which are used alone or in combination. Alternatively, the compound of the formula (VI) can be used in excess amount as a solvent without using the above-described solvents.

The reaction temperature is optionally selected between 20° and 300° C., with 40° to 200° C. being preferable.

The reaction time is not particularly limited.

Concentration of the thus-obtained reaction mixture gives the compound of the formula (VII) and/or (VIII) in good yield and, if necessary, the compound can be further purified by distillation. However, isolation and purification of the compound of the formula (VII) and/or (VIII) are not particularly necessary for obtaining the final end product of the formula (IX). Taking into account the stability of the compound, it is desirable to use the reaction mixture per se or the concentrated residue in the subsequent step.

Oxidation and/or hydrolysis reaction is applied to the synthesis of, as the final and end product, the aromatic aldehyde represented by the formula (IX) from the compound of the formula (VII) and/or (VIII) (step 5). Where the benzyl halide derivative represented by the formula (VII) is used as a starting material or as a major ingredient thereof, oxidation reaction is applied and, where the benzal halide derivative represented by the formula (VIII) is used as a starting material or as a major component thereof, hydrolysis reaction is applied. Also, where a mixture of the compound of the formula (VII) and the compound of the formula (VIII) is used as a starting material, both oxidation reaction and hydrolysis reaction are conducted.

As the oxidizing process, there are illustrated, for example, the following ones:

(1) A process of using hexamethylenetetramine.
(2) A process of oxidizing with a compound having a nitro or nitroso group (for example, 2-nitropropane, nitrobenzene, p-nitrosodimethylaniline, dinitrogen tetraoxide, etc.).
(3) A process of using dimethyl sulfoxide.
(4) A process of oxidizing with a metal oxidizing agent (for example, potassium bichromate, sodium bichromate, ammonium cerium nitrate, potassium permanganate, chromic anhydride, etc.).

Typical examples of these processes will be described below.

Process (1) of using hexamethylenetetramine (Sommelet reaction) comprises reacting the starting compound with hexamethylenetetramine to form a hexanium salt, followed by hydrolyzing in the presence or absence of an acid to form the aromatic aldehyde of the formula (IX).

Hexamethylenetetramine is used in an amount of 0.8 to 4 mols, preferably 0.8 to 2.5 mols, per mol of the starting material.

As the acid, there are illustrated aliphatic carboxylic acids (e.g., formic acid, acetic acid, propionic acid, etc.), mineral acids (e.g., hydrochloric acid, sulfuric acid, phosphoric acid, etc.), and organic sulfonic acids (e.g., toluenesulfonic acid, methanesulfonic acid, etc.).

These acids are preferably used in amounts of not less than 1 mol per mol of hexamethylenetetramine. Of course, they may be used in less amounts or may not be used.

Solvents for this reaction are not particularly limited, and any one that is inert to the reaction may be used. Solvents are generally used by mixing with water which is necessary for the hydrolysis. As the solvents, there are illustrated organic carboxylic acids, alcohols, aromatic hydrocarbons, aliphatic hydrocarbons, and halogenated hydrocarbons, such as acetic acid, formic acid, propionic acid, methanol, ethanol, propanol, benzene, diethyl ether, toluene, carbon tetrachloride, hexane, etc.

The reaction temperature is optionally selected between 10° and 200° C., with 20° to 170° C. being preferable.

Process (2) of using a compound containing a nitro or nitroso group, for example, 2-nitropropane, is conducted by reacting a metal salt of 2-nitropropane with the starting material in a solvent.

The metal salt of 2-nitropropane is prepared by adding 2-nitropropane to a reaction solvent containing a base in an amount of 0.4 to 1.3 mols per mol of 2-nitropropane at 0° to 150° C. The base to be used here means a metal such as lithium, sodium or potassium, an alcoholate thereof, or a metal hydride such as lithium hydride or sodium hydride. The reaction solvent is not particularly limited, and any one that is inert to the reaction can be used. 2-Nitropropane as the reactant can also be used as a solvent.

The reaction between the metal salt of 2-nitropropane and the starting compound is conducted by adding the starting compound to the metal salt at 0° to 150° C., and reacting for 0.5 to 10 hours. The intended aromatic aldehyde of the formula (IX) can be obtained usually by further hydrolyzing with water at 0° to 200° C.

In this reaction, the molar ratio of the metal salt of 2-nitropropane to the starting compound is usually 0.9:1 to 3.0:1.

Process (3) of using dimethyl sulfoxide comprises reacting dimethyl sulfoxide with the starting compound in the presence or absence of an acid-binding agent to form the aromatic aldehyde of the formula (IX).

Dimethyl sulfoxide is used in an amount of at least one mol per mol of the halide compound, with not less than 2 mols being preferable.

As the acid-binding agent, there are illustrated, for example, alkali metal hydroxides, alkali metal carbonates, alkali metal hydrogencarbonates, metal carboxylates, metal sulfonates, tertiary amines, etc., with the alkali metal hydrogencarbonates (e.g., sodium hydrogencarbonate, potassium hydrogencarbonate, etc.) being preferred. These are used in optional amounts of from 0.05 to 5 mols per mol of the halide compound. However, the reaction may be conducted without using the acid-binding agent.

Solvents for this reaction are not particularly limited, and any one that is inert to the reaction may be used. Alternatively, excess dimethyl sulfoxide may be used as a solvent.

The reaction temperature is optionally selected between 0° and 200° C., with 10° to 180° C. being preferable.

Process (4) of using a metal oxidizing agent, particularly ammonium cerium nitrate, comprises reacting the halide compound represented by the formula (VII) and/or (VIII) with ammonium cerium nitrate in the presence or absence of an acidic catalyst to form the aromatic aldehyde of the formula (IX).

Ammonium cerium nitrate is used in an optional amount between 1 and 10 mols per mol of the halide compound, with 1.2 mols to 7 mols being preferable.

As the acidic catalyst, there are illustrated, for example, acetic acid, formic acid, propionic acid, hydrochloric acid, sulfuric acid, nitric acid, perchloric acid, etc. These are preferably used in amounts of from 0.05 to 30 mols per mol of ammonium cerium nitrate, with the amounts of more than 30 mols being employable. Also, they may be used as solvents. The reaction can proceed even in the absence of the acidic catalyst.

Solvents are not particularly limited, and any one that is inert to the reaction may be used. Alternatively, the above-described acidic catalyst may be used as a solvent.

The reaction temperature is optionally selected between 10° and 250° C., with 20° to 160° C. being preferable.

Other oxidizing agents, such as potassium bichromate, sodium bichromate, potassium permanganate and chromic anhydride can be used in the same manner as with ammonium cerium nitrate.

The hydrolysis reaction will be described below.

This hydrolysis reaction is conducted by reacting the starting compound with water in the presence or absence of the catalyst.

In using the catalyst, examples of the catalyst include bases such as alkali metal hydroxides, alkali metal carbonates, alkali metal hydrogencarbonates, metal carboxylates, tertiary amines, morpholine, etc., and acids such as formic acid, acetic acid, propionic acid, hydrochloric acid, sulfuric acid, hydrobromic acid, etc. These are usually used in amounts of from 0.05 to 5 mols per mol of the starting compound, though this range not being limitative.

In this reaction, reaction solvents are not particularly necessary, and presence of water is sufficient. However, solvents inert to the reaction may be used or, in some cases, the acids may be used as solvents as well as catalysts together with water.

The reaction temperature is usually in the range of from 0° to 350° C., with 10° to 250° C. being preferable.

Thus, the hydrolysis reaction can be conducted.

In effecting both the oxidation reaction and the hydrolysis reaction, processes capable of effecting the hydrolysis reaction upon conducting the oxidation reaction, for example, process (1), are employed. With process (4), the two reactions can be effected by allowing water to copresent as the reaction solvent. Process (2) also permits to conduct the two reactions.

The aromatic aldehyde of the formula (IX) can be obtained in good yield from the thus-obtained reaction mixture through general procedures such as concentration, liquid separation, steam distillation, distillation, crystallization, etc.

As the thus-obtained compound of the formula (IX), there are illustrated, for example, 3,4-methylenedioxybenzaldehyde (heliotropin), 3,4-ethylenedioxy-benzaldehyde, 3,4-propylenedioxy-benzaldehyde, 3,4-dimethoxy-benzaldehyde, 3,4-diethoxy-benzaldehyde, 3,4-dipropoxy-benzaldehyde, 3-methoxy-4-hydroxybenzaldehyde, 3-ethoxy-4-hydroxy-benzaldehyde, 3-propoxy-4-hydroxy-benzaldehyde, 3-hydroxy-4-methoxy-benzaldehyde, 3-hydroxy-4-ethoxy-benzaldehyde, 3-hydroxy-4-propoxy-benzaldehyde, 3-methoxy-4-ethoxy-benzaldehyde, 3-methoxy-4-propoxy-benzaldehyde, 3-ethoxy-4-methoxy-benzaldehyde, 3-ethoxy-4-propoxy-benzaldehyde, 3-propoxy-4-methoxy-benzaldehyde, 3-propoxy-4-ethoxy-benzaldehyde, etc.

The present invention will now be described in more detail by reference to the following examples which, however, do not limit the present invention in any way.

EXAMPLE 1

1.0 mol of an m- and p-cresol mixture (m-/p-=6/4) (I-1), 4.0 mols of acetic anhydride, and 0.005 mol of sulfuric acid were reacted for 1 hour under reflux condition. After completion of the reaction, unreacted acetic anhydride and acetic acid formed as a by-product were distilled off to quantitatively obtain cresol acetate (IV-1).

Then, to 1.0 mol of the thus-obtained compound (IV-1) was added 1.3 mols of aluminum chloride at 90° to 110° C. over 2 hours, followed by elevating the temperature and continuing stirring for 2 hours at 160° to 170° C. After completion of the reaction, the reaction mixture was cooled to 100° C., and decomposed with a 10% hydrochloric acid aqueous solution. After extracting with toluene, the toluene was distilled off from the resulting organic layer to obtain 2-hydroxy-4- and -5-methylacetophenone (III-1) in 90% yield.

0.8 mol of the thus-obtained compound (III-1) and 0.9 mol of 30% hydrogen peroxide were dissolved in a mixture solvent composed of a 4-fold amount by weight of dioxane and a 4-fold amount by weight of water, based on (III-1). 0.9 mol of 30% sodium hydroxide was added dropwise thereto at 0° to 10° C. over 2 hours while blowing nitrogen thereinto. Stirring was further continued for 3 hours at the same temperature. After completion of the reaction, dilute hydrochloric acid was added to the reaction mixture to make it weakly acidic, followed by extraction with diethyl ether. Upon distilling off the solvent from the resulting organic layer, there was obtained 4-methylcatechol (V) in 94% yield.

Then, 0.7 mol of the thus-obtained compound (V) and 1.6 mols of sodium hydroxide were dissolved in a 1.5-fold amount by weight, based on the weight of (V), of water, and the solution was added dropwise to a solution composed of a 5-fold amount by weight of dimethyl sulfoxide and a 1.2-fold amount by weight of dichloromethane, the respective amounts being based on the weight of (V), at 90° to 100° C. under reflux condition. The dropwise addition took 3 hours. Water azeotropically discharged during the dropwise addition was separated off. The reaction was continued for 2 hours at the same temperature. After completion of the reaction, a 2.5-fold amount by weight, based on (V), of water was added to the reaction mixture, and 3,4-methylenedioxytoluene (VI-1) was distilled out as an azeotropic mixture. Yield was 92%.

Alternatively, a solution composed of 0.7 mol of the compound (V) obtained by the above process, 1.75 mols of sodium hydroxide, and a 2.8-fold amount by weight, based on (V), of water was added dropwise to a solution composed of a 1.6-fold amount by weight, based on (V), of water, 2.0 mols of dibromomethane, and 0.007 mol of tetra-n-butylammonium bromide over 5 hours under reflux condition. After completion of the dropwise addition, the mixture was maintained at the same temperature for 2 hours while stirring. After completion of the reaction, the reaction mixture was extracted with toluene and, after liquid separation, the toluene was distilled off from the resulting organic layer. Distillation of the residue gave 3,4-methylenedioxytoluene (VI-1) in 89% yield.

Then, 0.6 mol of the thus-obtained compound (VI-1) and 0.006 mol of benzoyl peroxide were dissolved in a 3.5-fold amount by weight, based on (VI-1), of carbon tetrachloride, and 0.66 mol of bromine gas was blown thereinto under reflux condition. The blowing time was 10 hours. After completion of the reaction, the solvent was distilled off to obtain 3,4-methylenedioxybenzyl bromide (VII-1) in 90% yield.

0.5 mol of the thus-obtained compound (VII-1) was added dropwise to 0.75 mol of sodium bicarbonate and a 3-fold amount by weight, based on (VII-1), of dimethyl sulfoxide at 20° to 30° C., followed by stirring at the same temperature for 4 hours. Then, the reactants were reacted for 5 hours at 70° to 80° C. After completion of the reaction, the reaction mixture was poured into water and, after extraction with diethyl ether and liquid separation, the diethyl ether was distilled off from the resulting organic layer. Distillation of the concentrated residue gave heliotropin (b.p. 131° to 135° C./10 mmHg) in 79% yield.

EXAMPLE 2

1.0 mol of the same m- and p-cresol mixture as used in Example 1 (I-1), 1.0 mol of acetyl chloride, and 2.2 mols of titanium tetrachloride were reacted in nitrobenzene at 70° C. for 6 hours. After completion of the reaction, steam distillation of the reaction mixture gave the end product of 2-hydroxy-4- and -5-methylacetophenone (III-1) in 85% yield.

Then, 0.9 mol of 30% sodium hydroxide was added to a mixture solution composed of 0.8 mol of the thus-obtained compound (III-1), 0.9 mol of 30% hydrogen peroxide, 0.008 mol of tetra-n-butylammonium bromide, a 2-fold amount by weight of methyl isobutyl ketone, a 2.7-fold amount by weight of water, and a 0.2-fold amount by weight of pyridine, the respective amounts being based on the weight of (III-1), at 0° to 10° C. over 3 hours. Stirring was continued for 3 hours at the same temperature. After completion of the reaction, the reaction mixture was rendered weakly acidic with hydrochloric acid, followed by extracting with methyl isobutyl ketone. After liquid separation, the methyl isobutyl ketone was distilled off from the organic layer to obtain 4-methylcatechol (V) in 93% yield.

Then, 0.7 mol of the thus-obtained compound (V) and 1.75 mols of sodium hydroxide were dissolved in a 5-fold amount by weight, based on (V), of water, and 1.75 mols of dimethylsulfate was added dropwise thereto at 60° to 70° C. over 2 hours. The mixture was maintained at the same temperature for 1 hour while stirring. After cooling, the organic layer was separated and distilled to obtain 3,4-dimethoxytoluene (VI-2) in 93% yield.

Then, 0.6 mol of the thus-obtained compound (VI-2) was dissolved in a 3.5-fold amount by weight, based on (VI-2), of carbon tetrachloride, and 0.66 mol of bromine gas was blown thereinto under reflux condition while irradiating with a mercury vapor lamp. The blowing was completed in 16 hours. After completion of the reaction, the solvent was distilled off to obtain 3,4-dimethoxybenzyl bromide (VII-2) in 92% yield.

0.5 mol of the thus-obtained compound (VII-2) was added dropwise to a 3.5-fold amount by weight, based on (VII-2), of a 50% acetic acid solution containing 0.75 mol hexamethylenetetramine over 1 hour at 20° to 30° C. After maintaining the mixture at the same temperature for 1 hour, the inside temperature was elevated to 105° to 110° C. and maintained at the same temperature for 4 hours. After completion of the reaction, the reaction mixture was poured into water, and extracted with toluene. The organic layer was concentrated, and distillation of the concentrated residue gave veratraldehyde (b.p. 155° C./10 mmHg) in 75% yield.

EXAMPLE 3

0.5 mol of the compound (VII-1) synthesized in the same manner as in Example 1 was dissolved in a 2-fold amount by weight, based on (VII-1), of dimethyl sulfoxide, and a solution composed of 1.0 mol of sodium ethylate, 1.1 mols of 2-nitropropane, and a 3-fold amount by weight, based on sodium ethylate, of ethanol was added dropwise thereto at 20° to 30° C. over 2 hours. The mixture was maintained at the same temperature for 10 hours while stirring. After completion of the reaction, the reaction mixture was rendered weakly acidic with hydrochloric acid, poured into water, and extracted with toluene. The resulting organic layer was concentrated, and distillation of the concentrated residue gave heliotropin (b.p. 131° to 134° C./10 mmHg) in 65% yield.

EXAMPLES 4 TO 7

Results obtained by following the abovedescribed Examples are tabulated below.

|  |  | Example 4 | Example 5 | Example 6 | Example 7 |
|---|---|---|---|---|---|
| Step 1 | Starting Material (I) | p-cresol | p-cresol | p-cresol | m-/p-cresol mixture |
|  | Reaction Conditions | same as in Example 1 | same as in Example 1 | same as in Example 1 | same as in Example 1 |
|  | Yield (%) | 93 | 93 | 93 | 90 |
| Step 2 | Reaction Conditions | same as in Example 1 | same as in Example 1 | same as in Example 1 | same as in Example 2 |
|  | Yield (%) | 94 | 94 | 94 | 92 |
| Step 3 | Alkylating Agent | diethylsulfate | n-propyl bromide | dimethylsulfate | dichloroethane |
|  | Reaction Conditions | same as in Example 2 | same as in the alternative process in Example 1 | same as in Example 2 | same as in Example 1 |
|  | Yield (%) | 90 | 92 | 85 | 90 |
| Step 4 | Reaction Conditions | same as in Example 2 | same as in Example 2 | same as in Example 2 | same as in Example 2 |
|  | Yield (%) | 91 | 92 | 90 | 90 |

| | Example 4 | Example 5 | Example 6 | Example 7 |
|---|---|---|---|---|
| Step 5 Reaction Conditions | same as in Example 1 | same as in Example 2 | same as in Example 1 | same as in Example 1 |
| Yield (%) | 78 | 73 | 70 | 74 |
| End Product | 3,4-diethoxy-benzaldehyde | 3,4-di-n-propoxy-benzaldehyde | 3-methoxy-4-hydroxy-benzaldehyde | 3,4-ethylenedioxy-benzaldehyde |

EXAMPLE 8

1.2 mols of an m- and p-cresol mixture (m-/p-=6/4) (I-1), 2.0 mols of acetic anhydride, and 0.01 mol of pyridine were reacted for 2 hours under reflux condition. After completion of the reaction, unreacted acetic anhydride and acetic acid formed as a by-product were distilled off to quantitatively obtain cresol acetate (IV-1).

Then, 1 mol of the thus-obtained compound (IV-1) was dissolved in the same amount by weight of tetrachloroethane, and 0.8 mol of aluminum chloride was added thereto over 1 hour at 120° to 130° C. Thereafter, stirring was continued for 5 hours at the same temperature. After completion of the reaction, the reaction mixture was cooled to 30° C., and decomposed with water. 2-Hydroxy-4- and -5-methylacetophenone (III-1) was obtained in the organic layer in 92% yield.

Then, 0.9 mol of 30% sodium hydroxide was added dropwise, at 0° to 10° C., to a mixture solution composed of a tetrachloroethane solution containing 0.8 mol of the thus-obtained compound (III-1), 0.9 mol of 30% hydrogen peroxide, a 2-fold amount by weight, based on (III-1), of water, and a 0.3-fold amount by weight, based on (III-1), of pyridine over 2 hours. Stirring was continued at the same temperature for 3 hours. After completion of the reaction, the reaction mixture was rendered weakly acidic with hydrochloric acid, then separated into the organic layer and the aqueous layer. The aqueous layer was extracted with tetrachloroethane, and the extract was combined with the organic layer, followed by distilling off the tetrachloroethane to obtain 4-methylcatechol (V) in 96% yield.

0.75 mol of the thus obtained compound (V) and 1.6 mols of sodium hydroxide were dissolved in a 1.5-fold amount by weight, based on (V), of water, then added dropwise to a solution composed of a 6-fold amount by weight, based on (V), of dimethyl sulfoxide and 1.8 mols of dichloromethane at 90° C. to 100° C. The dropwise addition was completed in 3 hours. Water azeotropically discharged during the dropwise addition was separated off. The reaction was continued for 3 hours at the same temperature. After completion of the reaction, a 2.5-fold amount by weight, based on the reaction mixture, of water was added thereto, and 3,4-methylenedioxytoluene (VI-1) was distilled out as an azeotropic mixture. Yield: 93%.

Then, 0.6 mol of the thus-obtained compound (VI-1) and 0.01 mol of benzoyl peroxide were dissolved in a 3-fold amount by weight, based on (VI-1), of chlorobenzene, and 0.84 mol of bromine gas was blown thereinto under reflux condition. The blowing was completed in 10 hours. After completion of the reaction, the solvent was distilled off to obtain a mixture of 3,4-methylenedioxybenzyl bromide (VII-1) and 3,4-methylenedioxybenzal bromide (VIII-1) in 93.5% yield.

0.5 mol of the thus-obtained compounds (VII-1 plus VIII-1) were added dropwise, at 30° to 40° C., to a 3-fold amount by weight, based on (VII-1 plus VIII-1), of a 50% acetic acid solution containing 0.6 mol hexamethylenetetramine over 1 hour. After maintaining at the same temperature for 1 hour, the inside temperature was elevated to 90° to 100° C., and maintained at the same temperature for 4 hours. After completion of the reaction, the reaction mixture was poured into water, and extracted with toluene. The organic layer was concentrated, and distillation of the concentrated residue gave heliotropin (b.p. 131° to 135° C./10 mmHg) in 80% yield.

EXAMPLE 9

0.5 mol of 3,4-dimethoxytoluene (VI-2) obtained by synthesizing in the same manner as in Example 2 was dissolved in a 3-fold amount by weight, based on (VI-2), of chlorobenzene, and 0.005 mol of sodium bicarbonate and 0.01 mol of benzoyl peroxide were added thereto. Then, 0.53 mol of bromine gas was blown thereinto under reflux condition. The blowing was completed in 8 hours. After completion of the reaction, the solvent was distilled off to obtain 3,4-dimethoxybenzyl bromide (VII-2) in 92% yield.

Then, 0.4 mol of the thus-obtained compound (VII-2) was added dropwise to a 3-fold amount by weight, based on (VII-2), of dimethyl sulfoxide containing 0.5 mol of potassium hydrogencarbonate at 25° to 35° C. The dropwise addition was completed in 1.5 hours. Stirring was continued for 5 hours at the same temperature. Thereafter, the inside temperature was elevated to 60° to 70° C. to react for 4 hours. After completion of the reaction, the reaction mixture was poured into water, and extracted with diethyl ether, followed by distilling off the diethyl ether from the organic layer to obtain veratraldehyde in 82% yield.

While the invention has been described in detail and with reference to specific embodiments thereof, it will be apparent to one skilled in the art that various changes and modifications can be made therein without departing from the spirit and scope thereof.

What is claimed is:

1. A process for preparing an aromatic aldehyde represented by the following general formula:

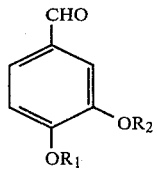

wherein $R_1$ and $R_2$ each represents a hydrogen atom or a lower alkyl group or $R_1$ and $R_2$ may jointly form an alkylene group, provided that $R_1$ and $R_2$ do not represent a hydrogen atom at the same time,
which comprises oxidizing 2-hydroxy-4-methylacetophenone and/or 2-hydroxy-5-methylacetophenone with hydrogen peroxide and an alkali in a heterogeneous solvent system of a water-insoluble or slightly water-soluble organic solvent and water in the presence of a catalyst to obtain 4-methylcatechol, condensing the 4-methylcatechol with an alkylating agent to obtain a methylbenzene derivative represented by the following general formula:

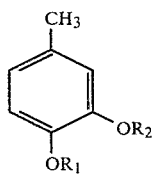

wherein $R_1$ and $R_2$ are the same as defined above, halogenating the methylbenzene derivative to obtain a halide compound represented by the following general formula:

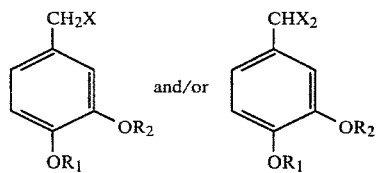

wherein $R_1$ and $R_2$ are the same as defined above, and X represents a halogen atom, and
oxidizing and/or hydrolyzing the halide compound.

2. A process for preparing an aromatic aldehyde represented by the following general formula:

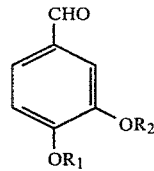

wherein $R_1$ and $R_2$ each represents a hydrogen atom or a lower alkyl group or $R_1$ and $R_2$ may jointly form an alkylene group, provided that $R_1$ and $R_2$ do not represent a hydrogen atom at the same time,
which comprises condensing m- and/or p-cresol with an acetic acid derivative represented by the following general formula:

CH₃COA wherein A represents a hydroxy group, a halogen atom, or —OCOCH₃,
to obtain 2-hydroxy-4-methylacetophenone and/or 2-hydroxy-5-methylacetophenone, or reacting m- and/or p-cresol with the acetic acid derivative to obtain m- and/or p-methylphenyl acetate and rearranging in at least one solvent selected from tetrachloroethane, chlorobenzene and toluene using aluminum chloride as a catalyst at a temperature of 80° to 160° C. to obtain 2-hydroxy-4-methylacetophenone and/or 2-hydroxy-5-methylacetophenone, oxidizing the 2-hydroxy-4-methylacetophenone and/or 2-hydroxy-5-methylacetophenone with hydrogen peroxide and an alkali in a heterogeneous solvent system of a water-insoluble or slightly water-soluble organic solvent and water in the presence of a catalyst to obtain 4-methylcatechol, condensing the 4-methylcatechol with an alkylating agent to obtain a methylbenzene derivative represented by the following general formula:

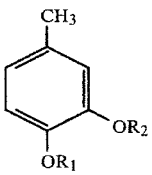

wherein $R_1$ and $R_2$ are the same as defined above, halogenating the methylbenzene derivative to obtain a halide compound represented by the following general formula:

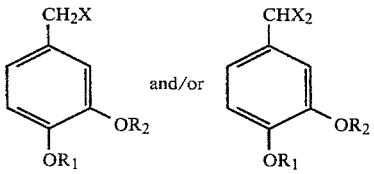

wherein $R_1$ and $R_2$ are the same as defined above, and X represents a halogen atom, and
oxidizing and/or hydrolyzing the halide compound.

3. A process according to claim 1 or 2, wherein the halogenation of the methylbenzene derivative is carried out in a halogenated hydrocarbon solvent.

4. A process according to claim 1 or 2, wherein the halogenation of the methylbenzene derivative is carried out in carbon tetrachloride, tetrachloroethane, dichloroethane or chlorobenzene.

5. A process according to claim 1 or 2, wherein the halogenation of the methylbenzene derivative is carried out in the presence of a radical-generating agent.

6. A process according to claim 1 or 2, wherein the halogenation of the methylbenzene derivative is carried out upon irradiation with light.

7. A process according to claim 1 or 2, wherein the halogenation of the methylbenzene derivative is carried out using a promotor selected from sodium carbonate, potassium carbonate, sodium hydrogencarbonate, potassium hydrogencarbonate and pyridine.

8. A process according to claim 1 or 2, wherein X is a bromine atom.

9. A process according to claim 1 or 2, wherein the oxidation and/or hydrolysis of the halide compound is carried out using hexamethylenetetramine.

10. A process according to claim 1 or 2, wherein the oxidation and/or hydrolysis of the halide compound is carried out using hexamethylenetetramine in an aqueous alcohol having 1 to 3 carbon atoms, or an aqueous carboxylic acid solvent having 1 to 3 carbon atoms.

11. A process according to claim 1 or 2, wherein the oxidation and/or hydrolysis of the halide compound is carried out using dimethyl sulfoxide in the presence or absence of an acid-binding agent.

12. A process according to claim 1 or 2, wherein the oxidation and/or hydrolysis of the halide compound is carried out using dimethyl sulfoxide in an alkali metal carbonate or an alkali metal hydrogencarbonate.

13. A process according to claim 1 or 2, wherein the oxidation and/or hydrolysis of the halide compound is carried out using dimethyl sulfoxide in sodium hydrogencarbonate or potassium hydrogencarbonate.

14. A process according to claim 1 or 2, wherein the aromatic aldehyde is heliotropin.

15. A process according to claim 1 or 2, wherein the aromatic aldehyde is veratraldehyde.

* * * * *